US011344482B2

(12) United States Patent
Bonnamy et al.

(10) Patent No.: US 11,344,482 B2
(45) Date of Patent: May 31, 2022

(54) AEROSOL DEVICE FOR PIGMENT DYEING BASED ON A PARTICULAR ACRYLIC POLYMER AND A SILICONE COMPOUND, DYEING PROCESS

(71) Applicant: L'OREAL, Paris (FR)

(72) Inventors: Arnaud Bonnamy, Saint-Ouen (FR); Ludivine Masselin, Saint-Ouen (FR); Karen Teboul, Saint-Ouen (FR)

(73) Assignee: L'OREAL, Paris (FR)

( * ) Notice: Subject to any disclaimer, the term of this patent is extended or adjusted under 35 U.S.C. 154(b) by 88 days.

(21) Appl. No.: 16/647,815

(22) PCT Filed: Sep. 27, 2018

(86) PCT No.: PCT/EP2018/076317
§ 371 (c)(1),
(2) Date: Mar. 16, 2020

(87) PCT Pub. No.: WO2019/063716
PCT Pub. Date: Apr. 4, 2019

(65) Prior Publication Data
US 2020/0268620 A1    Aug. 27, 2020

(30) Foreign Application Priority Data
Sep. 28, 2017  (FR) ...................................... 1758990

(51) Int. Cl.
*A61Q 5/06*   (2006.01)
*A61K 8/04*   (2006.01)
(Continued)

(52) U.S. Cl.
CPC ................ *A61K 8/046* (2013.01); *A61K 8/19* (2013.01); *A61K 8/25* (2013.01); *A61K 8/29* (2013.01);
(Continued)

(58) Field of Classification Search
CPC ...... A61Q 5/065; A61K 8/19; A61K 2800/43; A61K 8/8152; A61K 8/046; A61K 8/585;
(Continued)

(56) References Cited

U.S. PATENT DOCUMENTS 3,917,121 A   11/1975  Ciaffone
4,185,087 A    1/1980  Morlino
(Continued)

FOREIGN PATENT DOCUMENTS

EP    0095238 A2   11/1983
EP    0530974 A1    3/1993
(Continued)

OTHER PUBLICATIONS

International Search Report for counterpart Application No. PCT/EP2018/076317, dated Nov. 14, 2018.
(Continued)

*Primary Examiner* — Eisa B Elhilo
(74) *Attorney, Agent, or Firm* — The Marbury Law Group, PLLC (57) ABSTRACT

The present invention relates to an aerosol device comprising a composition for dyeing keratin fibres, comprising at least one aqueous dispersion of particles of hybrid, film-forming, hydrophobic acrylic polymer, at least one silicone compound chosen from linear silicone block copolymers and amino silicones, and at least one pigment. The invention also relates to a dyeing process in which said composition is applied to keratin fibres, the operation optionally being followed by drying. The composition makes it possible to obtain a coloured coating, which is persistent with respect to shampooing operations, leaving the treated fibres individualized, with an improved cosmetic feel.

20 Claims, 1 Drawing Sheet

B    A    C (51) Int. Cl.
*A61K 8/19* (2006.01)
*A61K 8/25* (2006.01)
*A61K 8/29* (2006.01)
*A61K 8/81* (2006.01)
*A61K 8/895* (2006.01)
*A61K 8/898* (2006.01)
*A45D 7/00* (2006.01)

(52) U.S. Cl.
CPC .......... *A61K 8/8152* (2013.01); *A61K 8/895* (2013.01); *A61K 8/898* (2013.01); *A61Q 5/065* (2013.01); *A45D 2007/001* (2013.01); *A61K 2800/43* (2013.01); *A61K 2800/87* (2013.01)

(58) Field of Classification Search
CPC .............. A61K 8/25; A61K 2800/87; A61K 2800/594; A61K 8/89; A61K 8/895; A61K 8/898; A45D 2007/001
USPC ............................................................ 8/407
See application file for complete search history.

(56) References Cited

U.S. PATENT DOCUMENTS

| | | | |
|---|---|---|---|
| 4,578,266 A | 3/1986 | Tietjen et al. | |
| 4,720,046 A | 1/1988 | Morane | |
| 5,645,609 A | 7/1997 | Andrean et al. | |
| 5,990,479 A | 11/1999 | Weiss et al. | |
| 6,106,577 A | 8/2000 | Audousset et al. | |
| 6,225,198 B1 | 5/2001 | Alivisatos et al. | |
| 10,159,639 B2 | 12/2018 | Teboul | |
| 10,532,021 B2 | 1/2020 | Teboul | |
| 2002/0010969 A1* | 1/2002 | Goettel | A61Q 5/065 8/405 |
| 2004/0142831 A1 | 7/2004 | Jager Lezer | |
| 2006/0085924 A1 | 4/2006 | Brun | |
| 2015/0132243 A1 | 5/2015 | Teboul | |
| 2015/0164196 A1 | 6/2015 | Teboul et al. | |
| 2015/0174041 A1* | 6/2015 | Teboul | A61K 8/895 424/70.6 |

FOREIGN PATENT DOCUMENTS

| | | | | |
|---|---|---|---|---|
| EP | 0874017 | A2 | 10/1998 | |
| EP | 1184426 | A2 | 3/2002 | |
| EP | 1400234 | A1 | 3/2004 | |
| EP | 1649898 | A2 | 4/2006 | |
| FR | 2679771 | A1 | 2/1993 | |
| FR | 2741530 | A1 | 5/1997 | |
| FR | 2984096 | A1 | 6/2013 | |
| FR | 2984132 | A1 | 6/2013 | |
| FR | 2984142 | A1 | 6/2013 | |
| FR | 2984143 | A1 | 6/2013 | |
| FR | 2992558 | A1 | 1/2014 | |
| FR | 3007285 | A1 | 12/2014 | |
| FR | 3007287 | A1 | 12/2014 | |
| JP | 05-17710 | U | 3/1993 | |
| JP | 07-258460 | A | 10/1995 | |
| JP | 09-188830 | A | 7/1997 | |
| JP | 10-158450 | A | 6/1998 | |
| JP | 10-158451 | A | 6/1998 | |
| WO | 00/76880 | | 12/2000 | |
| WO | 2013/092379 | A1 | 6/2013 | |
| WO | 2013/092381 | A1 | 6/2013 | |
| WO | 2014/001390 | A1 | 1/2014 | |
| WO | 2014/001391 | A1 | 1/2014 | |
| WO | 2014/202653 | A1 | 12/2014 | |
| WO | 2014/202655 | A1 | 12/2014 | |
| WO | 2014/202658 | A1 | 12/2014 | |
| WO | WO 2014202653 | A1 * | 12/2014 | ............... A61K 8/81 |

OTHER PUBLICATIONS

Dabbousi, B.O., et al., "(CdSe)ZnS Core-Shell Quantum Dots: Synthesis and Characterization of a Size Series of Highly Luminescent Nanocrystallites," Journal of Physical Chemistry B, vol. 101, 1997, pp. 9463-9475.

Peng, Xiaogang et al., "Epitaxial Growth of Highly Luminescent CdSe/CdS Core/Shell Nanocrystals with Photostability and Electronic Accessibility," Journal of the American Chemical Society, vol. 119, No. 30, 1997, pp. 7019-7029.

Translation of Notice of Reasons for Refusal for counterpart JP Application No. 2020-517344, dated Mar. 15, 2021.

Schlossman, Mitchell L., "Treated Pigments," Cosmetics and Toiletries, vol. 105, Feb. 1990, pp. 53-64.

* cited by examiner

B        A        C

AEROSOL DEVICE FOR PIGMENT DYEING BASED ON A PARTICULAR ACRYLIC POLYMER AND A SILICONE COMPOUND, DYEING PROCESS

CROSS REFERENCE TO RELATED APPLICATION

This is a national stage application of PCT/EP2018/076317, filed internationally on Sep. 27, 2018, which claims priority to French Application No. 1758990, filed on Sep. 28, 2017, which are incorporated by reference herein in their entireties.

The subject of the present invention is an aerosol device comprising a dyeing composition, in particular for dyeing keratin materials, comprising an aqueous dispersion of particles of a particular acrylic polymer, a particular silicone compound and a pigment, and also a dyeing process using said composition.

In the field of dyeing keratin materials, in particular keratin fibres, in particular human keratin fibres, it is already known practice to dye keratin fibres via various techniques using direct dyes or pigments for non-permanent dyeing, or dye precursors for permanent dyeing.

Non-permanent dyeing or direct dyeing consists in dyeing keratin fibres with dyeing compositions containing direct dyes. These dyes are coloured and colouring molecules that have affinity for keratin fibres. They are applied to the keratin fibres for a time necessary to obtain the desired colouring, and are then rinsed out.

The standard dyes that are used are, in particular, dyes of the nitrobenzene, anthraquinone, nitropyridine, azo, xanthene, acridine, azine or triarylmethane type, or natural dyes.

Some of these dyes may be used under lightening conditions, which enables the production of colourings that are visible on dark hair.

It is also known practice to dye keratin fibres permanently via oxidation dyeing. This dyeing technique consists in applying to the keratin fibres a composition containing dye precursors such as oxidation bases and couplers. Under the action of an oxidizing agent, these precursors will form one or more coloured substances in the hair.

The variety of molecules used as oxidation bases and couplers allows a wide range of colours to be obtained, and the colourings resulting therefrom are permanent, strong and resistant to external agents, especially to light, bad weather, washing, perspiration and rubbing.

In order to be visible on dark hair, these two dyeing techniques require prior or simultaneous bleaching of the keratin fibres. This bleaching step, performed with an oxidizing agent such as hydrogen peroxide or persalts, results in appreciable degradation of the keratin fibres, which impairs their cosmetic properties. The hair then has a tendency to become coarse, more difficult to disentangle and more brittle.

Another dyeing method consists in using pigments. Specifically, the use of pigment on the surface of keratin fibres generally makes it possible to obtain visible colourings on dark hair, since the surface pigment masks the natural colour of the fibre. The use of pigment for dyeing keratin fibres is described, for example, in patent application FR 2 741 530, which recommends using for the temporary dyeing of keratin fibres a composition comprising at least one dispersion of film-forming polymer particles comprising at least one acid function and at least one pigment dispersed in the continuous phase of said dispersion.

The colourings obtained via this dyeing method have the drawback of having a low resistance to shampoos.

It is moreover known practice to colour coat the hair using a composition comprising an electrophilic monomer of cyanoacrylate type, and a pigment, in particular in document EP 1 649 898. Such a composition makes it possible to obtain perfectly coated and non-greasy hair. However, the coating obtained is not entirely satisfactory in the face of external agents such as washing and perspiration. Moreover, the coating obtained is sensitive to fatty substances such as sebum.

It is also possible to dye the hair (coloured coating) using a pressure-sensitive adhesive silicone copolymer, in particular a copolymer based on silicone resin and on fluid silicone. Once deposited on the hair, these copolymers exhibit the advantage of contributing persistent colour. On the other hand, the treated hair is somewhat harsh to the touch.

Thus, the aim of the present invention is to develop a device for dyeing keratin materials, in particular keratin fibres, in particular human keratin fibres such as the hair, which allows fast and easy application of the composition to the keratin fibres, makes it possible to obtain a uniform and smooth coloured coating on the whole of the head of hair, and perfectly individualized strands of hair, while at the same time forming a coating which is persistent with respect to shampooing operations and to various attacks that the hair might suffer, without degradation of the keratin fibres. Furthermore, the hair retains a natural feel.

This aim is achieved with the present invention, a subject of which is an aerosol device comprising:
   at least one pressurized container comprising:
      a) at least one composition comprising at least one aqueous dispersion of particles of hybrid, film-forming, hydrophobic acrylic polymer, at least one silicone compound chosen from linear silicone block copolymers and amino silicones, and at least one pigment,
      b) at least one propellant, and
   a means for delivering the composition.

A subject of the invention is also a process for dyeing keratin materials, in particular keratin fibres, in particular human keratin fibres such as the hair, comprising the application to said keratin materials of a composition delivered from a device as defined above, optionally followed by drying.

The term "at least one" is intended to mean "one or more".

The term "comprising a" is intended to mean "comprising at least one", unless otherwise specified.

By using such a composition, coloured deposits or coatings are rapidly obtained on the keratin materials, in particular on the keratin fibres, in particular human keratin fibres such as the hair, said coloured deposits or coatings making it possible to obtain a visible colouring on all types of hair in a manner persistent with respect to shampooing operations, while at the same time preserving the physical qualities of the keratin fibre. Such a coating is, in particular, resistant to the external attacking factors to which the hair may be subjected, such as blow-drying and perspiration. It makes it possible in particular to obtain a smooth and uniform deposit. Moreover, it has been noted, surprisingly, that the hair remains perfectly individualized, and can be styled without any problem, and that the styling properties given to the fibre are persistent with respect to shampooing operations.

The term "individualized strands of hair" is intended to mean strands of hair which, after application of the composition and drying, are not stuck together (or are all separate from each other) and therefore do not form clumps of hair, since the coating is formed around virtually every strand of hair.

The invention can be better understood on reading the detailed description which follows, and with reference to the following FIGURE in the example, in which.

DYEING COMPOSITION A

Aqueous Dispersion of Particles of Hydrophobic Film-Forming Hybrid Acrylic Polymer For the purposes of the invention, the term "polymer" is intended to mean a compound corresponding to the repetition of one or more units (these units resulting from compounds known as monomers). This or these unit(s) are repeated at least twice and preferably at least three times.

The term "film-forming" polymer is intended to mean a polymer capable of forming, by itself alone or in the presence of an auxiliary film-forming agent, a macroscopically continuous film on a support, in particular on keratin materials, and preferably a cohesive film.

The term "hydrophobic polymer" is intended to mean a polymer having a solubility in water at 25° C. of less than 1% by weight.

The dispersion can be a simple dispersion in the aqueous medium of the composition. The dispersion can also be an emulsion.

Mention may be made, as a specific case of dispersions, of latexes.

The term "hybrid acrylic" polymer is intended to mean, within the meaning of the present invention, a polymer synthesized from at least one compound (i) chosen from monomers having at least one optionally salified (meth) acrylic acid group and/or esters of these acid monomers and/or amides of these acid monomers and from at least one compound (ii) different from the compounds (i).

The (meth)acrylic acid group(s) of the compound i) can optionally be in the form of alkali metal, alkaline-earth metal or ammonium salt(s), or organic base salt(s).

The (meth)acrylic acid esters (also known as (meth) acrylates) are advantageously chosen from alkyl (meth) acrylates, in particular $C_1$-$C_{30}$, preferably $C_1$-$C_{20}$ and better still $C_1$-$C_{10}$ alkyl (meth)acrylates, aryl (meth)acrylates, in particular $C_6$-$C_{10}$ aryl (meth)acrylates, and hydroxyalkyl (meth)acrylates, in particular $C_2$-$C_6$ hydroxyalkyl (meth) acrylates.

Mention may be made, among alkyl (meth)acrylates, of methyl methacrylate, ethyl methacrylate, butyl methacrylate, isobutyl methacrylate, 2-ethylhexyl methacrylate, lauryl methacrylate or cyclohexyl methacrylate.

Mention may be made, among hydroxyalkyl (meth)acrylates, of hydroxyethyl acrylate, 2-hydroxypropyl acrylate, hydroxyethyl methacrylate or 2-hydroxypropyl methacrylate.

Mention may be made, among aryl (meth)acrylates, of benzyl acrylate and phenyl acrylate.

The (meth)acrylic acid esters which are particularly preferred are the alkyl (meth)acrylates.

According to the present invention, the alkyl group of the esters can be either fluorinated or perfluorinated, that is to say that a portion or all of the hydrogen atoms of the alkyl group are replaced by fluorine atoms.

Mention may be made, as amides of the acid monomers, for example, of (meth)acrylamides and in particular N-alkyl (meth)acrylamides, especially N—($C_2$-$C_{12}$ alkyl)(meth) acrylamides. Mention may be made, among the N-alkyl (meth)acrylamides, of N-ethylacrylamide, N-(t-butyl) acrylamide, N-(t-octyl)acrylamide and N-undecylacrylamide.

Mention will be made, as compounds (ii) different from the compounds (i), for example, of styrene monomers.

In particular, the acrylic polymer according to the invention can be a styrene/(meth)acrylate copolymer and especially a polymer chosen from copolymers resulting from the polymerization of at least one styrene monomer and at least one $C_1$-$C_{20}$, preferably $C_1$-$C_{10}$ alkyl (meth)acrylate monomer.

More particularly, the acrylic polymer according to the invention can be a copolymer resulting from the polymerization of at least one styrene monomer, of at least one $C_1$-$C_{20}$, preferably $C_1$-$C_{10}$, alkyl (meth)acrylate monomer and of at least one optionally salified (meth)acrylic acid monomer.

As styrene monomers that may be used in the invention, examples that may be mentioned include styrene and α-methylstyrene, preferably styrene.

The $C_1$-$C_{10}$ alkyl acrylate monomer can be chosen from methyl acrylate, ethyl acrylate, propyl acrylate, butyl acrylate, hexyl acrylate, octyl acrylate or 2-ethylhexyl acrylate.

Mention may be made, as acrylic polymer synthesized with styrene compound, of the styrene/(meth)acrylate copolymers sold under the name Joncryl 77 by BASF, under the name Yodosol GH41F by Akzo Nobel and under the name Syntran 5760 CG by Interpolymer.

Mention may also be made, as compound (ii), of the compounds which interact via a process other than the radical polymerization of unsaturated compounds or the compounds resulting from such a process. Such a process can, for example, be a polycondensation. Mention may be made, as polycondensation, of the formation of polyurethanes, polyesters or polyamides. Besides the acrylic monomer(s), the hybrid hydrophobic film-forming polymer of the invention will then contain the compound derived from the condensation process or the compounds that interact in the polycondensation process.

Mention may in particular be made, as hydrophobic film-forming hybrid acrylic copolymers of this type, of that sold under the reference Hybridur 875 Polymer Dispersion by Air Products and Chemicals.

Use may also be made, as hydrophobic film-forming hybrid acrylic copolymer, of the product sold under the reference Primal HG 1000 by Dow.

The hydrophobic film-forming hybrid acrylic polymer or polymers in aqueous dispersion can be present in a content, as active material, ranging from 0.1% to 30% by weight, more particularly from 0.5% to 20% by weight and preferably from 1% to 15% by weight, with respect to the total weight of the composition.

a) Silicone Compound

The composition according to the invention comprises at least one silicone compound chosen from linear silicone block copolymers, amino silicones other than linear silicone block copolymers, and mixtures thereof.

Linear Silicone Block Copolymer

The silicone copolymer used in the composition according to the invention is a linear block copolymer, that is to say a non-crosslinked copolymer, obtained by chain extension and not by crosslinking.

The term "block copolymer" (or "sequential copolymer") denotes a polymer comprising at least two distinct blocks (sequences). Each block of the polymer results from one type of monomer or from several different types of monomer. This means that each block can be composed of a homopolymer or a copolymer; this copolymer constituting the block which can in turn be random or alternating.

It should also be noted that the copolymer is "linear", in other words the structure of the polymer is neither branched, nor star-shaped, nor grafted.

The linear silicone block copolymer is advantageously provided in the form of particles in dispersion in an aqueous medium.

The aqueous dispersion of block copolymer particles is a silicone-in-water (Sil/W) emulsion, the oil globules of which are constituted of a silicone of high viscosity, such that these globules appear to form "flexible particles".

The size of the linear silicone block copolymer particles can vary widely. Preferably, in the present patent application, the linear silicone block copolymer particles generally exhibit a number-average size of less than or equal to 2 microns and preferably of less than or equal to 1 micron.

The aqueous dispersions of linear silicone block copolymer particles used in the composition according to the invention can be chosen in particular from those described in the document EP-A-874 017, the teaching of which is incorporated herein by reference. According to this document, it is possible in particular to obtain the silicone copolymers constituting these particles by a chain-extension reaction, in the presence of a catalyst, starting from at least:
(a) a polysiloxane (i) having at least one reactive group and preferably one or two reactive groups per molecule; and
(b) an organosilicone compound (ii) which reacts with the polysiloxane (i) via a chain-extension reaction.

In particular, the polysiloxane (i) is chosen from the compounds of formula (I):

in which $R_1$ and $R_2$ represent, independently of one another, a hydrocarbon group having from 1 to 20 carbon atoms and preferably from 1 to 10 carbon atoms, such as methyl, ethyl, propyl or butyl, or an aryl group, such as phenyl, or a reactive group, and n is an integer greater than 1, provided that there are on average between one and two reactive groups per polymer.

The term "reactive group" is intended to mean any group that is capable of reacting with the organosilicon compound (ii) to form a block copolymer. Mention may be made, as reactive groups, of hydrogen; aliphatically unsaturated groups, in particular vinyl, allyl or hexanyl groups; the hydroxyl group; alkoxy groups, such as methoxy, ethoxy or propoxy groups; alkoxyalkoxy groups; the acetoxy group; amino groups, and mixtures thereof. Preferably, more than 90% and better still more than 98% of the reactive groups are at the chain end, that is to say that the $R_2$ radicals generally constitute more than 90% and even 98% of the reactive groups.

n can in particular be an integer ranging from 2 to 100, preferably from 10 to 30 and better still from 15 to 25.

The polysiloxanes having formula (I) are linear polymers, that is to say comprising few branches and generally less than 2 mol % of siloxane units. Moreover, the $R_1$ and $R_2$ groups can optionally be substituted by amino groups, epoxy groups, groups comprising sulfur, silicon or oxygen.

Preferably, at least 80% of the $R_1$ groups are alkyl groups and better still methyl groups.

Preferably, the reactive $R_2$ group at the chain end is an aliphatically unsaturated group and in particular a vinyl group.

Mention may in particular be made, as polysiloxanes (i), of dimethylvinylsiloxypolydimethylsiloxane, compound of formula (I) in which the $R_1$ radicals are methyl radicals and the $R_2$ radicals at the chain end are vinyl radicals, whereas the two other $R_2$ radicals are methyl radicals.

The organosilicone compound (ii) can be chosen from the polysiloxanes having formula (I) or the compounds which act as chain extenders. If it is a compound having formula (I), the polysiloxane (i) will comprise a first reactive group and the organosilicon compound (ii) will comprise a second reactive group which will react with the first group. If it is a chain extender, it can be a silane, a siloxane (disiloxane or trisiloxane) or a silazane. Preferably, the organosilicone compound (ii) is a liquid organohydropolysiloxane having formula (II):

where n is an integer greater than 1 and preferably greater than 10, for example ranging from 2 to 100, preferably from 10 to 30 and better still from 15 to 25. According to a specific embodiment of the invention, n is equal to 20.

The silicone block copolymers used according to the invention are advantageously devoid of oxyalkylene group(s), in particular devoid of oxyethylene and/or oxypropylene groups.

The catalyst for the reaction between the polysiloxane and the organosilicon compound may be chosen from metals and especially from platinum, rhodium, tin, titanium, copper and lead. It is preferably platinum or rhodium.

The silicone copolymer particle dispersion used in the composition according to the invention may especially be obtained, for example, by mixing (a) water, (b) at least one emulsifier, (c) the polysiloxane (i), (d) the organosilicon compound (ii) and (e) a catalyst. Preferably, one of the constituents (c), (d) or (e) is added last to the mixture, in order for the chain-extension reaction to begin only in the dispersion.

Mention may be made, as emulsifiers capable of being used in the preparation process described above in order to obtain the aqueous dispersion of particles, of non-ionic or ionic (anionic, cationic or amphoteric) emulsifiers. They are preferably non-ionic emulsifiers which can be chosen from polyalkylene glycol ethers of a fatty alcohol comprising from 8 to 30 carbon atoms and preferably from 10 to 22 carbon atoms; polyoxyalkylenated and in particular polyoxyethylenated sorbitan alkyl esters, where the alkyl substituent comprises from 8 to 30 carbon atoms and preferably from 10 to 22 carbon atoms; polyoxyalkylenated and in particular polyoxyethylenated alkyl esters, where the alkyl radical comprises from 8 to 30 carbon atoms and preferably from 10 to 22 carbon atoms; polyethylene glycols; polypropylene glycols; diethylene glycols; and mixtures thereof.

The amount of emulsifier(s) is generally from 1% to 30% by weight, with respect to the total weight of the reaction mixture.

The emulsifier used in order to obtain the aqueous dispersion of particles is preferably chosen from polyethylene glycol ethers of fatty alcohols and their mixtures, and in particular polyethylene glycol ethers of alcohols comprising an alcohol of 12 or 13 carbon atoms and from 2 to 100 oxyethylene units and preferably from 3 to 50 oxyethylene units, and mixtures thereof. Mention may be made, for example, of $C_{12}$-$C_{13}$ Pareth-3, $C_{12}$-$C_{13}$ Pareth-23 and mixtures thereof.

According to a specific embodiment of the invention, the dispersion of silicone copolymer particles is obtained from dimethylvinylsiloxypolydimethylsiloxane (or divinyl dimethicone) as compound (i) and from the compound of formula (II) with preferably n=20 as compound (ii), preferably in the presence of a catalyst of platinum type, and the dispersion of particles is preferably obtained in the presence of $C_{12}$-$C_{13}$ Pareth-3 and $C_{12}$-$C_{13}$ Pareth-23 as emulsifiers.

Use may in particular be made, as dispersion of silicone copolymer particles, of the product sold under the name HMW 2220 by Dow Corning (CTFA name: divinyl dimethicone/dimethicone copolymer/$C_{12}$-$C_{13}$ Pareth-3/$C_{12}$-$C_{13}$ Pareth-23), which is a 60% aqueous dispersion of divinyl dimethicone/dimethicone copolymer comprising $C_{12}$-$C_{13}$ Pareth-3 and $C_{12}$-$C_{13}$ Pareth-23, said dispersion comprising approximately 60% by weight of copolymer, 2.8% by weight of $C_{12}$-$C_{13}$ Pareth-23, 2% by weight of $C_{12}$-$C_{13}$ Pareth-3 and 0.31% by weight of preservatives, the remainder to 100% being water.

Amino Silicone

According to the invention, the term "amino silicone" denotes any silicone comprising at least one primary, secondary or tertiary amine or one quaternary ammonium and more particularly at least one primary amine.

The amino silicones used in the composition according to the present invention can be chosen from the silicones of formula (I) below:

in which:

T is a hydrogen atom, a phenyl radical, a hydroxyl (—OH) radical, a $C_1$-$C_8$ alkyl radical, preferably a methyl radical, or a $C_1$-$C_8$ alkoxy radical, more preferably a methyl radical, a denotes the number 0 or an integer from 1 to 3, and preferably 0, b denotes 0 or 1, and in particular 1, m and n are numbers such that the sum (n+m) can vary in particular from 1 to 2000 and especially from 50 to 150, n denotes a number from 0 to 1999 and in particular from 49 to 149 and m denotes a number from 1 to 2000 and in particular from 1 to 10, $R_1$ is a monovalent radical of formula —$C_qH_{2q}$L in which q is a number from 2 to 8, it being possible for one or more hydrogen atoms to be replaced by a hydroxyl group, and L is an optionally quaternized amino group chosen from the groups:

—N($R^2$)—$CH_2$—$CH_2$—N($R'^2$)$_2$;
—N($R^2$)$_2$;
—$N^+$($R^2$)$_3$$Q^-$;
—$N^+$($R^2$)(H)$_2$$Q^-$;
—$N^+$($R^2$)$_2$H$Q^-$;
—N($R^2$)—$CH_2$—$CH_2$—$N^+$($R'^2$)(H)$_2$$Q^-$, in which $R_2$ and $R'_2$ denote a hydrogen atom, a phenyl, a benzyl or a saturated monovalent hydrocarbon radical, for example a $C_1$-$C_{20}$ alkyl radical, and $Q^-$ represents an anion, such as, for example, fluoride, chloride, bromide or iodide.

In particular, the amino silicones corresponding to the definition of the formula (I) are chosen from the compounds corresponding to the formula below:

in which

R, R' and R", which are identical or different, denote a $C_1$-$C_4$ alkyl, preferably $CH_3$, radical, a $C_1$-$C_4$ alkoxy, preferably methoxy, radical or an OH radical;

A represents a linear or branched $C_3$-$C_8$, preferably $C_3$-$C_6$, alkylene radical, and m and n are integers which depend on the molecular weight and the sum of which is between 1 and 2000.

According to a first possibility, R, R' and R", which are identical or different, represent a $C_1$-$C_4$ alkyl, preferably methyl, radical or a hydroxyl radical, A represents a $C_1$-$C_8$, preferably $C_3$-$C_4$, alkylene radical, and m and n are such that the weight-average molecular weight of the compound is between 5000 and 500 000 approximately. The compounds of this type are named "amodimethicone" in the CTFA dictionary.

According to a second possibility, R, R' and R", which may be identical or different, represent a $C_1$-$C_4$ alkoxy or hydroxyl radical, at least one of the R or R" radicals is an alkoxy radical and A represents a $C_3$ alkylene radical. The hydroxyl/alkoxy mole ratio is preferably between 0.2/1 and 0.4/1 and advantageously equal to 0.3/1. Moreover, m and n are such that the weight-average molecular weight of the compound is between 2000 and $10^6$. More particularly, n is between 0 and 999 and m is between 1 and 1000, the sum of n and m being between 1 and 1000.

In this category of compounds, mention may be made, inter alia, of the product Belsil® ADM 652 sold by Wacker.

According to a third possibility, R and R", which may be different, represent a $C_1$-$C_4$ alkoxy or hydroxyl radical, at least one of the R and R" radicals is an alkoxy radical, R' represents a methyl radical and A represents a $C_3$ alkylene radical. The hydroxyl/alkoxy mole ratio is preferably between 1/0.8 and 1/1.1 and advantageously is equal to 1/0.95. Moreover, m and n are such that the weight-average molecular weight of the compound is between 2000 and 200 000. More particularly, n is between 0 and 999 and m is between 1 and 1000, the sum of n and m being between 1 and 1000.

More particularly, mention may be made of the product Fluid WR® 1300 sold by Wacker.

The amino silicones used in the composition in accordance with the invention preferably have the general formula (III) below:

in which:

A denotes a linear or branched $C_2$-$C_8$ and preferably $C_2$-$C_8$, better still $C_3$, alkylene radical;

$R_1$ and $R_2$ denote, independently of one another, a $C_1$-$C_4$ alkyl, preferably methyl, radical or a $C_1$-$C_4$ alkoxy, preferably methoxy, radical or a hydroxyl radical, m and n are numbers such that the weight-average molecular weight (MW) is greater than or equal to 75 000.

Preferably, the radicals R1 are identical and denote a hydroxyl radical.

Preferably, the viscosity of the amino silicone is greater than 25 000 mm²/s, measured at 25° C.

More preferably, the viscosity of the amino silicone is between 30 000 and 200 000 mm²/s at 25° C. and more preferably still between 50 000 and 150 000 mm²/s, measured at 25° C., and better still from 70 000 to 120 000 mm²/s. The viscosities of the silicones are, for example, measured according to Standard ASTM 445, Appendix C.

Preferably, the cationic charge of the amino silicone is less than or equal to 0.5 meq/g, preferably ranging from 0.01 to 0.1 meq/g and better still from 0.03 to 0.06 meq/g.

Preferably, the amino silicone has a weight-average molecular weight ranging from 75 000 to 1 000 000 and more preferentially still ranging from 100 000 to 200 000.

The weight-average molecular weights of these amino silicones are measured by gel permeation chromatography (GPC) at ambient temperature, as polystyrene equivalents. The columns used are μ styragel columns. The eluent is THF and the flow rate is 1 ml/min. 200 μl of a 0.5% by weight solution of silicone in THF are injected. Detection is performed by refractometry and UV-metry.

A particularly preferred amino silicone corresponding to this formula (III) is, for example, the Xiameter MEM-8299® Emulsion from the company Dow Corning.

It is noted that the molecular mass of these silicones is determined by gel permeation chromatography (ambient temperature, polystyrene standard, μ styragem columns, eluent THF, flow rate of 1 mm/minute, 200 μl of a solution containing 0.5% by weight of silicone in THF are injected, and detection is performed by refractometry and UV-metry).

A product corresponding to the definition of the formula (I) is in particular the polymer called "trimethylsilylamodimethicone" in the CTFA dictionary, corresponding to formula (IV) below:

in which n and m have the meanings given above in accordance with the formula (II).

Such compounds are described, for example, in EP 95 238; a compound of formula (III) is sold, for example, under the name Q2-8220 by OSI.

Other amino silicones according to the invention are quaternized amino silicones, in particular:

(a) the compounds corresponding to formula (V) below:

in which:

R3 represents a C1-C18 alkyl radical, for example methyl;

R4 represents a divalent hydrocarbon-based radical, in particular a C1-C18 alkylene radical;

Q⁻ is an anion, in particular chloride;

r represents a mean statistical value from 2 to 20 and in particular from 2 to 8;

s represents a mean statistical value from 20 to 200 and in particular from 20 to 50.

Such compounds are described more particularly in U.S. Pat. No. 4,185,087.

A compound falling within this class is the product sold by the company Union Carbide under the name Ucar Silicone ALE 56.

(b) the quaternary ammonium silicones of formula (VI):

in which:

R7, which may be identical or different, represent a monovalent hydrocarbon-based radical containing from 1 to 8 carbon atoms and in particular a C1-C8 alkyl radical, for example methyl;

R6 represents a divalent hydrocarbon-based radical, especially a C1-C18 alkylene radical or a divalent C1-C18, and for example C1-C8, alkylenoxy radical linked to the Si via an SiC bond;

R8, which may be identical or different, represent a hydrogen atom, a monovalent hydrocarbon-based radical containing from 1 to 18 carbon atoms, and in particular a C1-C18 alkyl radical, a C2-C18 alkenyl radical or a radical —R6-NHCOR7;

$X^-$ is an anion, such as a halide ion, in particular chloride, or an organic acid salt (acetate, and the like);

r represents a mean statistical value from 2 to 200 and in particular from 5 to 100.

These silicones are described, for example, in patent application EP-A 0 530 974.

(c) the amino silicones of formula (VII):

in which:

R1, R2, R3 and R4, which may be identical or different, denote a C1-C4 alkyl radical or a phenyl group, R5 denotes a C1-C4 alkyl radical or a hydroxyl group, n is an integer ranging from 1 to 5, m is an integer ranging from 1 to 5, and in which x is selected such that the amine number is between 0.01 and 1 meq/g.

Preferably, the amino silicones of the invention are non-quaternized, that is to say that they do not comprise a nitrogen atom having a permanent charge (quaternary ammonium group).

Preferably, the amino silicones of the invention are not block polymers.

The silicones which are particularly preferred in accordance with the invention are the polysiloxanes comprising amino groups, such as amodimethicones or trimethylsilylamodimethicones, and in particular the compounds of formulae (II), (III) and (IV).

When the amino silicones of the invention are used, a particularly advantageous embodiment is their joint use with cationic and/or non-ionic surfactants.

Use may be made, by way of example, of the product sold under the name Cationic Emulsion DC 929 by Dow Corning, which comprises, in addition to amodimethicone, a cationic surfactant comprising a mixture of products corresponding to the formula:

in which $R^5$ denotes $C_{14}$-$C_{22}$ alkenyl and/or alkyl radicals derived from tallow fatty acids and known under the CTFA name tallowtrimonium chloride, in combination with a non-ionic surfactant of formula:

$C_9H_{19}$—$C_6H_4$—$(OC_2H_4)_{10}$—OH, known under the CTFA name Nonoxynol 10.

Use may also be made, for example, of the products sold under the names Xiameter MEM-0939 Emulsion and Xiameter MEM-0949 Emulsion by Dow Corning, which comprise, in addition to amodimethicone, a cationic surfactant which is trimethylcetylammonium chloride and a non-ionic surfactant of formula: $C_{13}H_{27}$—$(OC_2H_4)_{12}$—OH, known under the CTFA name Trideceth-12.

Mention may also be made of the product sold under the reference Belsil ADM 6060 by Wacker, which comprises, in addition to amodimethicone, a non-ionic surfactant Trideceth-10.

In particular, when these amino silicones are used, a particularly advantageous embodiment is their use in the form of an oil-in-water emulsion.

The oil-in-water emulsion comprises one or more surfactants. The surfactants may be of any nature, but are preferably cationic and/or non-ionic.

The silicone particles in the emulsion have a volume-average diameter D[4.3] generally ranging from 10 nm to 1000 nm, preferably from 50 nm to 800 nm, more particularly from 100 nm to 600 nm and even more particularly from 200 nm to 500 nm. These particle sizes may be determined especially using a laser granulometer, for example the Malvern Mastersizer 2000 granulometer.

According to the invention, all the silicones can also be used in the form of emulsions or microemulsions.

According to the invention, the silicone compound(s) may represent from 0.1% to 20% by weight, preferably from 0.5% to 15% by weight and more particularly from 0.1% to 10% by weight relative to the total weight of the composition.

According to one embodiment, the hybrid hydrophobic film-forming acrylic polymer(s) and the silicone compound(s) according to the invention are present in a weight ratio (as polymer active materials) of hydrophobic film-forming acrylic polymer(s) to silicone copolymer(s)

according to the invention ranging from 0.2 to 10, better still from 0.5 to 5 and even better still from 1 to 3.

When the hydrophobic film-forming hybrid acrylic polymer has a glass transition temperature which is too high for the desired use, a plasticizer may be combined therewith so as to lower this temperature of the mixture used. The plasticizer can be chosen from the plasticizers normally used in the field of application and in particular from the compounds which may be solvents for the polymer.

Preferably, the plasticizer has a molecular mass of less than or equal to 5000 g/mol, preferably less than or equal to 2000 g/mol, preferentially less than or equal to 1000 g/mol and more preferentially less than or equal to 900 g/mol. The plasticizer advantageously has a molecular weight of greater than or equal to 100 g/mol.

Thus, the composition can additionally comprise at least one plasticizer. In particular, mention may be made, alone or as a mixture, of the normal plasticizers, such as:

glycols and their derivatives, such as diethylene glycol ethyl ether, diethylene glycol methyl ether, diethylene glycol butyl ether or diethylene glycol hexyl ether, ethylene glycol ethyl ether, ethylene glycol butyl ether or ethylene glycol hexyl ether;

polyethylene glycols, polypropylene glycols, polyethylene glycol/polypropylene glycol copolymers and mixtures thereof, in particular high molecular weight polypropylene glycols, for example having a molecular weight ranging from 500 to 15 000, such as, for example, glycol esters;

propylene glycol derivatives and in particular propylene glycol phenyl ether, propylene glycol diacetate, dipropylene glycol ethyl ether, tripropylene glycol methyl ether and diethylene glycol methyl ether, dipropylene glycol butyl ether. Such compounds are sold by Dow Chemical under the names Dowanol PPH and Dowanol DPnB;

acid esters, in particular carboxylic acid esters, such as citrates, phthalates, adipates, carbonates, tartrates, phosphates or sebacates;

esters resulting from the reaction of a monocarboxylic acid of formula $R_{11}COOH$ with a diol of formula $HOR_{12}OH$ with $R_{11}$ and $R_{12}$, which are identical or different, representing a saturated or unsaturated and linear, branched or cyclic hydrocarbon chain preferably comprising from 3 to 15 carbon atoms and optionally comprising one or more heteroatoms, such as N, O or S, in particular the monoester resulting from the reaction of isobutyric acid and octanediol, such as 2,2,4-trimethyl-1,3-pentanediol, such as that sold under the reference Texanol Ester Alcohol by Eastman Chemical;

oxyethylenated derivatives, such as oxyethylenated oils, in particular vegetable oils, such as castor oil;

mixtures thereof.

More particularly, the plasticizer can be chosen from esters of at least one carboxylic acid comprising from 1 to 7 carbon atoms and of a polyol comprising at least 4 hydroxyl groups.

The polyol can be a cyclized or uncyclized monosaccharide-polyhydroxyaldehyde (aldose) or polyhydroxyketone (ketose). The polyol is preferably a monosaccharide cyclized in hemiacetal form.

The polyol can be a monosaccharide or a polysaccharide comprising from 1 to 10 monosaccharides, preferably from 1 to 4 monosaccharides and more preferably one or two monosaccharides. The polyol can be chosen from erythritol, xylitol, sorbitol, glucose, sucrose, lactose or maltose.

The polyol is preferably a disaccharide. Mention may be made, among the disaccharides, of sucrose (also known as α-D-glucopyranosyl-(1-2)-β-D-fructofuranose), lactose (also known as β-D-galactopyranosyl-(1-4)-β-D-glucopyranose) and maltose (also known as α-D-glucopyranosyl-(1-4)-β-D-glucopyranose), and preferably sucrose.

The ester can be composed of a polyol esterified by at least two different monocarboxylic acids or by at least three different monocarboxylic acids.

The ester can be a copolymer of two esters, in particular a copolymer i) of a sucrose substituted by benzoyl groups and ii) of a sucrose substituted by acetyl and/or isobutyryl groups.

The carboxylic acid is preferably a monocarboxylic acid comprising from 1 to 7 carbon atoms and preferably from 1 to 5 carbon atoms, for example chosen from acetic acid, n-propanoic acid, isopropanoic acid, n-butanoic acid, isobutanoic acid, tert-butanoic acid, n-pentanoic acid and benzoic acid.

The ester can be obtained from at least two different monocarboxylic acids. According to one embodiment, the acid is an unsubstituted linear or branched acid.

The acid is preferably chosen from acetic acid, isobutyric acid, benzoic acid and mixtures thereof.

According to a preferred embodiment, the ester is sucrose diacetate hexa(2-methylpropanoate), such as that sold under the name Sustane SAIB Food Grade Kosher by Eastman Chemical.

According to another embodiment, the plasticizer can be chosen from esters of an aliphatic or aromatic polycarboxylic acid and of an aliphatic or aromatic alcohol comprising from 1 to 10 carbon atoms.

The aliphatic or aromatic alcohol comprises from 1 to 10 and preferably from 1 to 8 carbon atoms, for example from 1 to 6 carbon atoms. It can be chosen from R1OH alcohols such that R1 represents methyl, ethyl, propyl, isopropyl, butyl, hexyl, ethylhexyl, decyl, isodecyl, benzyl, or benzyl substituted by an alkyl comprising from 1 to 3 carbon atoms, and mixtures thereof.

The aliphatic or aromatic polycarboxylic acid preferably comprises from 3 to 12 carbon atoms, preferably from 3 to 10 carbon atoms and preferably from 3 to 8 carbon atoms, for example 6 or 8 carbon atoms.

The aliphatic or aromatic polycarboxylic acid is advantageously chosen from dicarboxylic acids and tricarboxylic acids.

Mention may be made, among the aliphatic dicarboxylic acids, of those of formula $HOOC-(CH_2)_n-COOH$, in which n is an integer ranging from 1 to 10 and preferably ranging from 2 to 8, for example equal to 2, 4, 6 or 8.

Dicarboxylic acids chosen from succinic acid, adipic acid and sebacic acid are preferred.

Mention may be made, among the aromatic dicarboxylic acids, of phthalic acid.

Mention may be made, among the tricarboxylic acids, of the triacids which correspond to the formula in which R represents an —H, —OH or —OCOR' group in which R' represents an alkyl group having from 1 to 6 carbon atoms. Preferably, R represents a —OCOCH$_3$ group.

The tricarboxylic acid is in particular chosen from acetylcitric acid, butyroylcitric acid or citric acid.

Among the tricarboxylic acid esters that may be used are esters derived from citric acid (or citrates) such as tributyl acetyl citrate, triethyl acetyl citrate, triethylhexyl acetyl citrate, trihexyl acetyl citrate, trihexyl butyroyl citrate, triisodecyl citrate, triisopropyl citrate, tributyl citrate and tris (2-ethylhexyl) citrate. Mention may be made, as commercial references of plasticizers mentioned above, of the Citroflex range sold by Vertellus, in particular Citroflex A4 and Citroflex C2.

Mention may be made, among the adipic acid esters, of dibutyl adipate and di(2-ethylhexyl) adipate.

Mention may be made, among the sebacic acid esters, of dibutyl sebacate, di(2-ethylhexyl) sebacate, diethyl sebacate and diisopropyl sebacate.

Mention may be made, among the succinic acid esters, of di(2-ethylhexyl) succinate and diethyl succinate.

Mention may be made, among the phthalic acid esters, of benzyl butyl phthalate, dibutyl phthalate, diethylhexyl phthalate, diethyl phthalate and dimethyl phthalate.

Advantageously, the plasticizer or plasticizers can be present in the composition in a content such that the weight ratio of the hydrophobic film-forming hybrid acrylic polymer or polymers to the plasticizer or plasticizers varies from 0.5 to 100, preferably from 1 to 50 and preferably from 1 to 10.

Pigments

The composition a) comprises one or more pigments.

Such a composition makes it possible to obtain coloured and persistent sheathings without damaging the keratin fibres. In addition, the use of the compositions according to the invention makes it possible, depending on the pigments used, to be able to obtain visible lightening of dark hair or else to obtain good coverage of dark hair, without degrading the hair.

The term "pigment" is intended to mean white or coloured particles of any shape which are insoluble in the composition in which they are present.

The pigments that may be used are especially chosen from the organic and/or mineral pigments known in the art, especially those described in Kirk-Othmer's Encyclopedia of Chemical Technology and in Ullmann's Encyclopedia of Industrial Chemistry.

They can be natural, of natural origin, or not.

These pigments may be in pigment powder or paste form. They may be coated or uncoated.

The pigments may be chosen, for example, from mineral pigments, organic pigments, lakes, pigments with special effects, such as nacres or glitter flakes, and mixtures thereof.

The pigment may be a mineral pigment. The term "mineral pigment" is intended to mean any pigment that satisfies the definition in Ullmann's encyclopedia in the chapter on inorganic pigments. Mention may be made, among mineral pigments of use in the present invention, of ochres, such as red ochre (clay (in particular kaolinite) and iron hydroxide (for example hematite)), brown ochre (clay (in particular kaolinite) and limonite) or yellow ochre (clay (in particular kaolinite) and goethite); titanium dioxide, optionally surface-treated; zirconium or cerium oxides; zinc, (black, yellow or red) iron or chromium oxides; manganese violet, ultramarine blue, chromium hydrate and ferric blue; or metal powders, such as aluminium powder or copper powder.

Mention may also be made of alkaline earth metal carbonates (such as calcium carbonate or magnesium carbonate), silicon dioxide, quartz and any other compound used as inert filler in cosmetic compositions, provided that these compounds contribute colour or whiteness to the composition under the conditions under which they are employed.

The pigment may be an organic pigment. The term "organic pigment" is intended to mean any pigment that satisfies the definition in Ullmann's encyclopedia in the chapter on organic pigments.

The organic pigment may especially be chosen from nitroso, nitro, azo, xanthene, pyrene, quinoline, anthraquinone, triphenylmethane, fluorane, phthalocyanine, metal-complex, isoindolinone, isoindoline, quinacridone, perinone, perylene, diketopyrrolopyrrole, indigo, thioindigo, dioxazine, triphenylmethane and quinophthalone compounds.

Use may also be made of any mineral or organic compound that is insoluble in the composition and standard in the cosmetics field, provided that these compounds give the composition colour or whiteness under the conditions under which they are used, for example guanine, which, according to the refractive index of the composition, is a pigment.

In particular, the white or coloured organic pigments can be chosen from carmine, carbon black, aniline black, azo yellow, quinacridone, phthalocyanine blue, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indole or phenol derivatives, as are described in Patent FR 2 679 771.

Mention may also be made, as example, of pigment pastes formed of organic pigment, such as the products sold by Hoechst under the names:

Cosmenyl Yellow I0G: Pigment Yellow 3 (CI 11710);
Cosmenyl Yellow G: Pigment Yellow 1 (CI 11680);
Cosmenyl Orange GR: Pigment Orange 43 (CI 71105);
Cosmenyl Red R: Pigment Red 4 (CI 12085);
Carmine Cosmenyl FB: Pigment Red 5 (CI 12490);
Cosmenyl Violet RL: Pigment Violet 23 (CI 51319);
Cosmenyl Blue A2R: Pigment Blue 15.1 (CI 74160);
Cosmenyl Green GG: Pigment Green 7 (CI 74260);
Cosmenyl Black R: Pigment Black 7 (CI 77266).

The pigments in accordance with the invention may also be in the form of composite pigments, as described in patent EP 1 184 426. These composite pigments may be composed especially of particles comprising a mineral core, at least one binder, which provides for the attachment of the organic pigments to the core, and at least one organic pigment which at least partially covers the core.

The organic pigment may also be a lake. The term "lake" is intended to mean dyes adsorbed onto insoluble particles, the assembly thus obtained remaining insoluble during use.

The inorganic substrates onto which the dyes are adsorbed are, for example, alumina, silica, calcium sodium borosilicate, calcium aluminium borosilicate and aluminium.

Mention may be made, among the dyes, of carminic acid. Mention may also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 1 O (CI 77 002), D&C Green 3 (CI 42 053), D&C Blue 1 (CI 42 090).

Mention may be made, as examples of lakes, of the product known under the following name: D&C Red 7 (CI 15 850:1).

The pigment may also be a pigment with special effects. The term "special effect pigments" is intended to mean pigments which generally create a coloured appearance (characterized by a certain shade, a certain vividness and a certain brightness) which is not uniform and which changes as a function of the conditions of observation (light, temperature, angles of observation, etc.). They thereby contrast with coloured pigments, which provide a conventional opaque, semi-transparent or transparent, uniform colour.

There exist several types of special effect pigments: those with a low refractive index, such as fluorescent, photochromic or thermochromic pigments, and those with a higher refractive index, such as nacres, interferential pigments or glitter.

Mention may be made, as examples of special effect pigments, of nacreous pigments, such as mica covered with titanium oxide or with bismuth oxychloride, coloured nacreous pigments, such as mica covered with titanium oxide and with iron oxides, mica covered with iron oxide, mica covered with titanium oxide and in particular with ferric blue or chromium oxide or mica covered with titanium oxide and with an organic pigment as defined above, and nacreous pigments based on bismuth oxychloride. Mention may be made, as nacreous pigments, of the following nacres: Cellini sold by Engelhard (mica-TiO$_2$-lake), Prestige sold by Eckart (mica-TiO$_2$), Prestige Bronze sold by Eckart (mica-Fe$_2$O$_3$) or Colorona sold by Merck (mica-TiO$_2$—Fe$_2$O$_3$).

Mention may also be made of the gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromelite); the nacres with a coppery glint sold especially by the company Engelhard under the name Copper 340A (Timica); the nacres with a red glint sold especially by the company Merck under the name Sienna fine (17386) (Colorona); the nacres with a yellow glint sold especially by the company Engelhard under the name Yellow (4502) (Chromelite); the red nacres with a gold glint sold especially by the company Engelhard under the name Sunstone G012 (Gemtone); the pink nacres sold especially by the company Engelhard under the name Tan opale G005 (Gemtone); the black nacres with a gold glint sold especially by the company Engelhard under the name Nu antique bronze 240 AB (Timica), the blue nacres sold especially by the company Merck under the name Matte blue (17433) (Microna), the white nacres with a silvery glint sold especially by the company Merck under the name Xirona Silver, and the golden-green pink-orange nacres sold especially by the company Merck under the name Indian summer (Xirona), and mixtures thereof.

Still as examples of nacres, mention may also be made of particles comprising a borosilicate substrate coated with titanium oxide.

Particles comprising a glass substrate coated with titanium oxide are sold in particular under the name Metashine MC1080RY by the company Toyal.

Finally, examples of nacres that may also be mentioned include polyethylene terephthalate flakes, especially those sold by the company Meadowbrook Inventions under the name Silver 1P 0.004×0.004 (silver flakes).

It is also possible to envisage multilayer pigments based on synthetic substrates, such as alumina, silica, calcium sodium borosilicate, calcium aluminium borosilicate and aluminium.

The special effect pigments can also be chosen from reflective particles, that is to say in particular particles having a size, a structure, in particular a thickness of the layer or layers of which it is composed and their physical and chemical nature, and a surface condition which allow them to reflect incident light. This reflection may, if appropriate, have an intensity sufficient to create, at the surface of the composition or mixture, when the latter is applied to the support to be made up, highlight points visible to the naked eye, that is to say more luminous points which contrast with their surroundings by appearing to sparkle.

The reflective particles can be selected so as not to detrimentally affect, to a significant extent, the colouring effect generated by the colouring agents which are combined with them and more particularly so as to optimize this effect in terms of colour rendition. They may more particularly have a yellow, pink, red, bronze, orange, brown, gold and/or coppery colour or glint.

These particles may have varied forms and may especially be in platelet or globular form, in particular in spherical form.

Irrespective of their form, the reflective particles may or may not have a multilayer structure, and, in the case of a multilayer structure, may have, for example, at least one layer of uniform thickness, especially of a reflective material.

When the reflective particles do not have a multilayer structure, they may be composed, for example, of metal oxides, especially titanium or iron oxides obtained synthetically.

When the reflective particles have a multilayer structure, they may comprise, for example, a natural or synthetic substrate, especially a synthetic substrate at least partially coated with at least one layer of a reflective material, especially of at least one metal or metallic material. The substrate may be made of one or more organic and/or mineral materials.

More particularly, it may be chosen from glasses, ceramics, graphite, metal oxides, aluminas, silicas, silicates, especially aluminosilicates and borosilicates, and synthetic mica, and mixtures thereof, this list not being limiting.

The reflective material may comprise a layer of metal or of a metallic material.

Reflective particles are described especially in documents JP-A-09188830, JP-A-10158450, JP-A-10158541, JP-A-07258460 and JP-A-05017710.

Again as an example of reflective particles comprising a mineral substrate coated with a layer of metal, mention may also be made of particles comprising a silver-coated borosilicate substrate.

Particles with a silver-coated glass substrate, in the form of platelets, are sold under the name Microglass Metashine REFSX 2025 PS by the company Toyal. Particles with a glass substrate coated with nickel/chromium/molybdenum alloy are sold under the name Crystal Star GF 550 and GF 2525 by this same company.

Use may also be made of particles comprising a metal substrate, such as silver, aluminium, iron, chromium, nickel, molybdenum, gold, copper, zinc, tin, magnesium, steel, bronze or titanium, said substrate being coated with at least one layer of at least one metal oxide, such as titanium oxide, aluminium oxide, iron oxide, cerium oxide, chromium oxide, silicon oxides and mixtures thereof.

Examples that may be mentioned include aluminium powder, bronze powder or copper powder coated with $SiO_2$ sold under the name Visionaire by the company Eckart.

Mention may also be made of pigments with an interference effect which are not attached to a substrate, such as liquid crystals (Helicones HC from Wacker) or interference holographic glitter flakes (Geometric Pigments or Spectra f/x from Spectratek). Pigments with special effects also comprise fluorescent pigments, whether these are substances that are fluorescent in daylight or that produce an ultraviolet fluorescence, phosphorescent pigments, photochromic pigments, thermochromic pigments and quantum dots, sold, for example, by the company Quantum Dots Corporation.

Quantum dots are luminescent semiconductive nanoparticles capable of emitting, under light excitation, irradiation with a wavelength of between 400 nm and 700 nm. These nanoparticles are known from the literature. In particular, they may be synthesized according to the processes described, for example, in U.S. Pat. No. 6,225,198 or 5,990,479, in the publications cited therein and also in the following publications: Dabboussi B. O. et al., "(CdSe)ZnS core-shell quantum dots: synthesis and characterization of a size series of highly luminescent nanocrystallites", Journal of Physical Chemistry B, vol. 101, 1997, pp. 9463-9475, and Peng, Xiaogang et al., "Epitaxial growth of highly luminescent CdSe/CdS core/shell nanocrystals with photostability and electronic accessibility", Journal of the American Chemical Society, vol. 119, No. 30, pages 7019-7029.

The variety of pigments that may be used in the present invention makes it possible to obtain a wide range of colours, and also particular optical effects such as metallic effects or interference effects.

The size of the pigment used in the cosmetic composition according to the present invention is generally between 10 nm and 200 µm, preferably between 20 nm and 80 µm and more preferably between 30 nm and 50 µm.

The pigments may be dispersed in the product by means of a dispersant.

The dispersant serves to protect the dispersed particles against agglomeration or flocculation. This dispersant may be a surfactant, an oligomer, a polymer or a mixture of several thereof, bearing one or more functionalities with strong affinity for the surface of the particles to be dispersed. In particular, they may become physically or chemically attached to the surface of the pigments. These dispersants also contain at least one functional group that is compatible with or soluble in the continuous medium. In particular, 12-hydroxystearic acid esters and $C_8$ to $C_{20}$ fatty acid esters of polyols such as glycerol or diglycerol are used, such as poly(12-hydroxystearic acid) stearate with a molecular weight of about 750 g/mol, such as the product sold under the name Solsperse 21 000 by the company Avecia, polyglyceryl-2 dipolyhydroxystearate (CTFA name) sold under the reference Dehymyls PGPH by the company Henkel, or poly-hydroxystearic acid such as the product sold under the reference Arlacel P100 by the company Uniqema, and mixtures thereof.

As other dispersants that may be used in the compositions of the invention, mention may be made of quaternary ammonium derivatives of polycondensed fatty acids, for instance Solsperse 17 000 sold by the company Avecia, and polydimethylsiloxane/oxypropylene mixtures such as those sold by the company Dow Corning under the references DC2-5185 and DC2-5225 C.

The pigments used in the cosmetic composition according to the invention may be surface-treated with an organic agent.

Thus, the pigments that have been surface-treated beforehand, which are useful in the context of the invention, are pigments that have totally or partially undergone a surface treatment of chemical, electronic, electrochemical, mechanochemical or mechanical nature, with an organic agent such as those described especially in Cosmetics and Toiletries, February 1990, Vol. 105, pages 53-64, before being dispersed in the composition in accordance with the invention. These organic agents may be chosen, for example, from waxes, for example carnauba wax and beeswax; fatty acids, fatty alcohols and derivatives thereof, such as stearic acid, hydroxystearic acid, stearyl alcohol, hydroxystearyl alcohol and lauric acid and derivatives thereof; anionic surfactants; lecithins; sodium, potassium, magnesium, iron, titanium, zinc or aluminium salts of fatty acids, for example aluminium stearate or laurate; metal alkoxides; polyethylene; (meth)acrylic polymers, for example polymethyl methacrylates; polymers and copolymers containing acrylate units; alkanolamines; silicone compounds, for example silicones, polydimethylsiloxanes; organofluorine compounds, for example perfluoroalkyl ethers; fluorosilicone compounds.

The surface-treated pigments that are useful in the cosmetic composition according to the invention may also have been treated with a mixture of these compounds and/or may have undergone several surface treatments.

The surface-treated pigments that are useful in the context of the present invention may be prepared according to surface-treatment techniques that are well known to those skilled in the art, or may be commercially available in the required form.

Preferably, the surface-treated pigments are coated with an organic layer.

The organic agent with which the pigments are treated may be deposited on the pigments by evaporation of solvent, chemical reaction between the molecules of the surface agent or creation of a covalent bond between the surface agent and the pigments.

The surface treatment may thus be performed, for example, by chemical reaction of a surface agent with the surface of the pigments and creation of a covalent bond between the surface agent and the pigments or the fillers. This method is especially described in U.S. Pat. No. 4,578,266.

An organic agent covalently bonded to the pigments will preferably be used.

The agent for the surface treatment may represent from 0.1% to 50% by weight, preferably from 0.5% to 30% by weight and even more preferentially from 1% to 10% by weight relative to the total weight of the surface-treated pigment.

Preferably, the surface treatments of the pigments are chosen from the following treatments:

a PEG-silicone treatment, for instance the AQ surface treatment sold by LCW;

a methicone treatment, for instance the SI surface treatment sold by LCW;

a dimethicone treatment, for instance the Covasil 3.05 surface treatment sold by LCW;

a dimethicone/trimethyl siloxysilicate treatment, for instance the Covasil 4.05 surface treatment sold by LCW;

a magnesium myristate treatment, for instance the MM surface treatment sold by LCW;

an aluminium dimyristate treatment, such as the MI surface treatment sold by Miyoshi;

a perfluoropolymethylisopropyl ether treatment, for instance the FHC surface treatment sold by LCW;

an isostearyl sebacate treatment, for instance the HS surface treatment sold by Miyoshi;

a perfluoroalkyl phosphate treatment, for instance the PF surface treatment sold by Daito;

an acrylate/dimethicone copolymer and perfluoroalkyl phosphate treatment, for instance the FSA surface treatment sold by Daito;

a polymethylhydrogenosiloxane/perfluoroalkyl phosphate treatment, for instance the FS01 surface treatment sold by Daito;

an acrylate/dimethicone copolymer treatment, for instance the ASC surface treatment sold by Daito;

an isopropyl titanium triisostearate treatment, for instance the ITT surface treatment sold by Daito;

an acrylate copolymer treatment, for instance the APD surface treatment sold by Daito;

a perfluoroalkyl phosphate/isopropyl titanium triisostearate treatment, for instance the PF+ITT surface treatment sold by Daito.

Preferably, the pigment is chosen from mineral or mixed mineral-organic pigments.

The amount of pigment(s) may range from 0.01% to 30% by weight, more particularly from 0.05% to 20% by weight and preferably from 0.1% to 15% by weight relative to the total weight of the composition.

The composition of the invention can comprise other coloured or colouring entities, such as direct dyes or dye precursors.

Thickener

According to a preferred embodiment, the composition according to the invention comprises at least one thickening agent chosen from polymeric or non-polymeric and inorganic or organic thickening agents, and mixtures thereof.

The term "thickener" is intended to mean a compound which modifies the rheology of the medium in which it is incorporated, by increasing its viscosity.

According to a specific embodiment of the invention, the composition comprises at least one inorganic thickener.

Preferably, the thickener or thickeners is/are chosen from fumed silica, clays or mixtures thereof.

The fumed silicas can be obtained by high-temperature pyrolysis of a volatile silicon compound in an oxhydric flame, producing a finely divided silica. This process makes it possible in particular to obtain hydrophilic silicas bearing a large number of silanol groups at their surface. Such hydrophilic silicas are sold, for example, under the names Aerosil 130®, Aerosil 200®, Aerosil 255®, Aerosil 300® and Aerosil 380® by Degussa and Cab-O-Sil HS-5®, Cab-O-Sil EH-5®, Cab-O-Sil LM-130®, Cab-O-Sil MS-55® and Cab-O-Sil M-5® by Cabot.

It is possible to chemically modify the surface of said silica via a chemical reaction which brings about a reduction in the number of silanol groups. It is especially possible to substitute silanol groups with hydrophobic groups: a hydrophobic silica is then obtained.

The hydrophobic groups may be:

trimethylsiloxyl groups, which are obtained in particular by treating fumed silica in the presence of hexamethyldisilazane. Silicas thus treated are known as Silica Silylate according to the CTFA (6th edition, 1995). They are sold, for example, under the references Aerosil R812® by Degussa and Cab-O-Sil TS-530® by Cabot.

dimethylsilyloxyl or polydimethylsiloxane groups, which are obtained in particular by treating fumed silica in the presence of polydimethylsiloxane or dimethyldichlorosilane. Silicas thus treated are known as "Silica dimethyl silylate" according to the CTFA (6th edition, 1995). They are sold, for example, under the references Aerosil R972® and Aerosil R974® by the company Degussa and Cab-O-Sil TS-610® and Cab-O-Sil TS-720® by the company Cabot.

The fumed silica preferably has a particle size that may be nanometric to micrometric, for example ranging from about 5 to 200 nm.

Clays are well-known products which are described, for example, in the publication Minéralogie des argiles [Mineralogy of Clays], S. Caillère, S. Hénin and M. Rautureau, 2nd Edition, 1982, Masson.

Clays are silicates including a cation which can be chosen from calcium, magnesium, aluminium, sodium, potassium or lithium cations, and mixtures thereof.

Examples of such products that may be mentioned include clays of the smectite family such as montmorillonites, hectorites, bentonites, beidellites and saponites, and also of the family of vermiculites, stevensite and chlorites.

These clays may be of natural or synthetic origin. Clays that are cosmetically compatible and acceptable with keratin materials are preferably used.

Mention may be made, as clay which can be used according to the invention, of synthetic hectorites (also known as laponites), such as the products sold by Laporte under the names Laponite XLG, Laponite RD and Laponite RDS (these products are sodium magnesium silicates and in particular lithium magnesium sodium silicates); bentonites, such as the product sold under the name Bentone HC by Rheox; magnesium aluminium silicates, in particular hydrated, such as the product sold by Vanderbilt Company under the name Veegum Ultra, or calcium silicates and in particular that in synthetic form sold by the company Fitz chem under the name Micro-Cel C.

The organophilic clay can be chosen from montmorillonite, bentonite, hectorite, attapulgite or sepiolite, and mixtures thereof. The clay is preferably a bentonite or a hectorite.

These clays may be modified with a chemical compound chosen from quaternary amines, tertiary amines, amine acetates, imidazolines, amine soaps, fatty sulfates, alkylaryl sulfonates and amine oxides, and mixtures thereof.

Mention may be made, as organophilic clays, of quaternium-18 bentonites, such as those sold under the names Bentone 3, Bentone 38 and Bentone 38V by Rheox, Tixogel VP by United Catalyst and Claytone 34, Claytone 40 and Claytone XL by Southern Clay; stearalkonium bentonites, such as those sold under the names Bentone 27 by Rheox, Tixogel LG by United Catalyst and Claytone AF and Claytone APA by Southern Clay; and quaternium-18/benzalkonium bentonites, such as those sold under the names Claytone HT and Claytone PS by Southern Clay.

The thickener can also be chosen from organic compounds.

Examples that may be mentioned include the following polymeric or non-polymeric products:

$C_{10}$-$C_{30}$ fatty amides, such as lauric diethanolamide, the polyglyceryl (meth)acrylate polymers sold under the Hispagel or Lubragel names by Hispano Quimica or Guardian, polyvinylpyrrolidone;

polyvinyl alcohol, crosslinked acrylamide polymers and copolymers, such as those sold under the names PAS 5161 or Bozepol C by Hoechst or Sepigel 305 by SEPPIC by Allied Colloid, or alternatively the crosslinked methacryloyloxyethyltrimethylammonium chloride homopolymers sold under the name Salcare SC95 by Allied Colloid, associative polymers and in particular such as associative polyurethanes or associative acrylic polymers the associative acrylic polymers being different from the hybrid, film-forming, hydrophobic acrylic polymers previously described. Such thickeners are in particular described in applications EP-A-1400234.

Preferably, the composition comprises at least one thickener chosen from mineral thickeners, more preferentially chosen from clays, and even more advantageously from smectites, and/or polymeric organic thickeners, more preferentially chosen from associative polymers, better still from associative acrylic polymers.

When it (they) is (are) present, the thickener(s) represent(s) a total content ranging from 0.1% to 10% by weight relative to the weight of the composition.

The composition according to the invention comprises water, which can preferably be present in a content ranging from 20% to 98% by weight, with respect to the weight of the composition.

The compositions may also contain at least one agent usually used in cosmetics, chosen, for example, from reducing agents, fatty substances, organic solvents or oils, softeners, antifoams, moisturizers, UV-screening agents, peptizers, solubilizers, anionic, cationic, non-ionic or amphoteric surfactants, proteins, vitamins, oxyethylenated or non-oxyethylenated waxes, paraffins, $C_{10}$-$C_{30}$ fatty acids such as stearic acid or lauric acid.

The above additives are generally present in an amount for each of them of between 0.01% and 20% by weight relative to the weight of the composition.

Needless to say, those skilled in the art will take care to choose this or these optional additive(s) so that the advantageous properties intrinsically attached to the formation of the sheathing in accordance with the invention are not, or not substantially, detrimentally affected.

The composition according to the invention may especially be in the form of a suspension, a dispersion, a gel, an emulsion, especially an oil-in-water (O/W) or water-in-oil (W/O) emulsion, or a multiple emulsion (W/O/W or polyol/O/W or O/W/O), in the form of a cream, a dispersion of vesicles, especially of ionic or non-ionic lipids, or a two-phase or multi-phase lotion.

Those skilled in the art may select the appropriate presentation form, and also the method for preparing it, on the basis of their general knowledge, taking into account first the nature of the constituents used, especially their solubility in the support, and secondly the application envisaged for the composition.

Device

The pressurized container comprises one or more propellants b)

The propellant(s) b) may optionally be present in the composition a) as previously described.

The container of the device according to the invention can have rigid walls and can directly contain the composition a).

As a variant, the container can have rigid walls and can contain a flexible-walled bag which contains the composition a).

According to this configuration, the composition a) in the bag may not comprise propellant b), the latter being in the volume defined between the rigid walls of the container and the bag.

Preferably, the composition a) contained in the bag itself also comprises at least one propellant b).

The device comprises a means for delivering the compositions, the means comprising at least one dispensing valve which surmounts the container.

The valve is in selective fluidic communication with the inside of the container via a valve inlet orifice, the communication being established in response to the activating of an activation means, such as a push-button.

When the device comprises a rigid-walled container which contains a flexible bag, the valve is then equipped with two inlet orifices, one of the orifices being able to communicate with the inside of the bag and the other being able to communicate with the volume defined between the bag and the rigid walls of the container.

When the container does not contain a bag, it is equipped with a dip tube which makes it possible to convey the composition to the inlet orifice of the dispensing valve.

When the container contains a bag, the inlet orifice of the valve opens into the bag.

The device can comprise at least one diffuser which caps the valve. The push-button may be part of the diffuser.

The diffuser may be equipped with one or more dispensing pipe(s) provided to convey the composition(s) up to one or more dispensing orifices.

Documents U.S. Pat. Nos. 3,917,121, 4,720,046 and WO 00/76880 disclose examples of devices.

The diffuser may comprise a single outlet orifice and diffusion branches that radiate from said orifice. As a variant, the diffuser comprises a plurality of outlet orifices. Advantageously, the outlet orifices may be arranged so as to obtain a diffusion grille.

Preferably, the container of the device according to the invention has rigid walls and directly contains the composition a).

Preferably, the composition a) comprises one or more propellants b).

It should be noted that, in the context of the invention, the propellant(s) can be used to enable the discharge of the composition(s), but also to facilitate or cause the frothing thereof.

The propellant(s) are present in the pressurized container according to the invention in a proportion of from 0.1% to 99% by weight, more preferentially from 1% to 96% by weight, relative to the total weight of the composition (packaged in the aerosol device). When the propellant(s) are present in the composition a), the total weight of the composition corresponds to the total weight of the composition a). When the propellant(s) are not present in the composition a), the total weight of the composition corresponds to the weight of the composition a) + the weight of the propellant(s).

According to one particular embodiment, the composition is dispensed in the form of a foam at the outlet of the aerosol device. In this embodiment, the propellant(s) are present in the pressurized container according to the invention in a proportion of from 0.1% to 25% by weight, more preferentially from 0.5% to 15% by weight, or even from 1% to 10% by weight, relative to the total weight of the composition (packaged in the aerosol device).

The propellant(s) is (are) in particular chosen from air, hydrocarbon-based gases, inert gases, and mixtures thereof. Mention may be made in particular of hydrocarbon-based gases, for instance propane, n-butane or isobutane, and mixtures thereof; fluoro gases, for instance chlorodifluoromethane, dichlorodifluoromethane, difluoroethane, chlorodifluoroethane, dichlorotetrafluoroethane, etc., and mixtures thereof; fluorohydrocarbon gases; dimethyl ether and mixtures of dimethyl ether with one or more hydrocarbon-based gases; nitrogen, air and carbon dioxide and mixtures thereof may also be used as inert propellant gases in the present invention.

Preferentially, the propellant(s) is (are) chosen from hydrocarbon-based gases containing from 2 to 6 carbon atoms, in particular isobutane, propane or n-butane and dimethyl ether, and mixtures thereof.

The gases are pressurized, more particularly at least partially pressurized in liquid form.

Advantageously, the dyeing composition which is dispensed from the pressurized container is in the form of a foam.

Process

The composition delivered by the aerosol device described above may be used on keratin materials, in particular wet or dry keratin fibres, and also on any type of fair or dark, natural or dyed, permanent-waved, bleached or relaxed fibres.

According to one particular embodiment of the process of the invention, the fibres are washed before application of the composition described above.

By virtue of the device according to the invention, the application is uniform on the whole of the head of hair.

The dyeing process is generally carried out at ambient temperature (between 15° C. and 25° C.).

After the application of the composition, the fibres can be left to dry or can be dried, for example at a temperature of greater than or equal to 30° C. According to a specific embodiment, this temperature is greater than 40° C. According to a specific embodiment, this temperature is greater than 45° C. and less than 220° C.

The drying, if it is employed, can be carried out immediately after application or after a leave-on time which can range from 1 minute to 30 minutes.

Preferably, if the fibres are dried, they are dried, in addition to a supply of heat, with a flow of air. This flow of air during the drying makes it possible to improve the individualization of the sheathing.

During drying, a mechanical action may be exerted on the locks, such as combing, brushing or running the fingers through. This operation may similarly be performed once the fibres have been dried, naturally or otherwise.

The drying step of the process of the invention may be performed with a hood, a hairdryer, a straightening iron, a Climazon, etc.

When the drying step is performed with a hood or a hairdryer, the drying temperature is between 40 and 110° C. and preferably between 50 and 90° C.

When the drying step is performed with a straightening iron, the drying temperature is between 110 and 220° C. and preferably between 140 and 200° C.

Once the drying is complete, a final rinsing or shampooing can optionally be carried out.

EXAMPLES

Example 1

|  | A | B |
|---|---|---|
| Styrene/acrylate/ammonium methacrylatecopolymer in aqueous dispersion, sold by Interpolymer under the name Syntran 5760 CG | 7.8 g AM | 7.8 g AM |
| Divinyl dimethicone/dimethicone copolymer as an aqueous emulsion, sold by Dow Corning under the reference HMW 2220 Non-ionic Emulsion | 4.7 g AM | 4.7 g AM |
| Magnesium aluminium silicate (Veegum R from Vanderbilt) | 1 g | 1 g |
| Synthetic mica coated with titanium dioxide/brown iron oxide (SYNCRYSTAL SOFT SILVER) | 8.5 g | — |
| Nacre of silica coated with brown iron oxide, sold by Merck under the name Xirona Le Rouge | — | 8.5 g |
| 1,2-octanediol | 0.9 g | 0.9 g |
| Butane | 5 g | 5 g |
| Preservative, fragrance | qs | qs |
| pH agent | qs pH 7.5 | qs pH 7.5 |
| Water | qs 100 g | qs 100 g |

AM: active material

Each of the compositions above is packaged in an aerosol container.

The compositions are dispensed in the form of a foam.

The composition A is applied to a lock of natural hair containing 90% grey hairs (NG90) of 1 g and to a lock of fair hair (tone depth 8) of 1 g, in a proportion of 0.4 g of composition/g of lock.

The composition B is applied to a lock of dark hair (tone depth 3) of 1 g and to a lock of fair hair (tone depth 8) of 1 g, in a proportion of 0.4 g of composition/g of lock.

The application is easy and uniform on the whole head of hair.

It is left to dry for a few seconds.

The strands of hair may be individualized with the fingers or by using a comb and/or a brush, and have a natural feel.

Colorimetric Evaluation:

The colours of the locks are evaluated in the CIE L* a* b* system, by means of a Konica Minolta CM2600d spectrocolorimeter (illuminant D65, angle 10°, specular component included) in which L* represents the strength of the colour, a* indicates the green/red colour axis and b* represents the blue/yellow colour axis.

The composition A makes it possible to obtain a yellow-removing effect, characterized by an increase in the lightness parameter L* (lightened hair) and a decrease in the parameter b* (hair less yellow).

|  |  | L* | b* |
|---|---|---|---|
| Before treatment | BN90 | 62.51 | 15.93 |
|  | HT8 | 43.31 | 17.68 |
| After treatment | BN90 | 68.58 | 11.32 |
|  | HT8 | 53.45 | 10.91 |

The composition B makes it possible to obtain a uniform vivid red colouring, which is persistent with respect to a few shampooing operations (visual evaluation).

Example 2

|  | C | D | E |
|---|---|---|---|
| Styrene/acrylate/ammonium methacrylate copolymer in aqueous dispersion, sold by Interpolymer under the name Syntran 5760 CG | — | 7.5 g AM | 7.8 g AM |
| Styrene/acrylate copolymer in aqueous dispersion, sold by BASF under the name Joncryl 77 | 8 g AM | — | — |
| Polydimethylsiloxane comprising aminoethyl aminopropyl groups, comprising methoxy and/or hydroxyl functions and α,ω silanols in a cationic emulsion (Xiameter MEM-8299 Emulsion from Dow Corning) | 4.5 g AM | — | — |
| Polydimethylsiloxane comprising aminoethyl aminopropyl groups, comprising methoxy and/or hydroxyl functions and α,ω silanols in a cationic emulsion containing 60% active materials (DC 2-8299, LC Cationic Emulsion from Dow Corning) | — | 4.5 g AM | — |
| Divinyl dimethicone/dimethicone copolymer as an aqueous emulsion, sold by Dow Corning under the reference HMW 2220 Non-ionic Emulsion | — | — | 4.7 g AM |
| Mica coated with brown, black iron oxides-titanium dioxide (Timica Nu-Antique Copper 340 AB from BASF) | — | — | 8.5 g |
| Black-2 and Laureth-21 (WD-CB2 from Daito) | 9.5 g | 9.5 g | — |
| Magnesium aluminium silicate (Veegum R from Vanderbilt) | — | — | 1 g |
| Butane | 5 g | 5 g | 5 g |
| 1,2-octanediol | — | — | 0.9 g |
| Preservative, fragrance | — | — | qs |
| pH agent | — | — | qs pH 7.5 |
| Water | qs 100 g | qs 100 g | qs 100 g |

Each of the compositions above is packaged in an aerosol container.

The compositions are dispensed in the form of a foam; each one is applied to a lock of natural hair containing 90% grey hairs (90NG) of 1 g in a proportion of 0.4 g of composition/g of lock.

The application is easy and uniform on the whole head of hair.

It is left to dry for a few seconds.

After application to the hair, the composition C makes it possible to obtain a chestnut brown shade completely covering the grey hairs. With the compositions D and E, a black cover with total coverage of the grey hairs is obtained.

The colour is uniform and persistent with respect to a few shampooing operations.

The strands of hair may be individualized with the fingers or by using a comb and/or a brush, and have a natural feel.

Example 3

| | |
|---|---|
| Styrene/acrylate/ammonium methacrylate copolymer in aqueous dispersion, sold by Interpolymer under the name Syntran 5760 CG | 7.4 g AM |
| Divinyl dimethicone/dimethicone copolymer as an aqueous emulsion, sold by Dow Corning under the reference HMW 2220 Non-ionic Emulsion | 4.7 g AM |
| Acrylate/beneth-25 methacrylate copolymer in an aqueous dispersion (Novethix L-10 polymer from Lubrizol) | 0.3 g AM |
| Nacre of mica coated with brown iron oxide, sold by Eckart under the name Prestige Soft Bronze | 8.5 g |
| 1,2-octanediol | 0.8 g |
| Butane | 10 g |
| Preservative, fragrance | qs |
| pH agent | qs pH 7.5 |
| Water | qs 100 g |

The composition above is packaged in an aerosol container.

It is dispensed in the form of a foam and is applied to a lock of dark hair (tone depth 3) of 1 g in a proportion of 0.4 g of composition/g of lock.

The application is easy and uniform on the whole head of hair.

It is left to dry for a few seconds.

A lightening of the hair (increase in the value L which characterizes the fairness) is obtained.

|  | L* |
|---|---|
| Before treatment | 20.93 |
| After treatment | 39.81 |

Example 4

Composition (g of AM for 100 g of composition)
AM: Active material

|  | F |
|---|---|
| Divinyl dimethicone/dimethicone copolymer as an aqueous emulsion, sold by Dow Corning under the reference HMW 2220 Non-ionic Emulsion | 4.94 AM |
| Styrene/acrylate/ammonium methacrylate copolymer in aqueous dispersion, sold by Interpolymer under the name Syntran 5760 CG | 8.2 AM |
| Magnesium aluminium silicate | 1 |
| Nacre of mica coated with brown iron oxide, sold by Eckart under the name Prestige Soft Bronze | 8 |
| water | Qs 100 g |

Device no 1 of the invention: aerosol container
The composition above is packaged in an aerosol container (aluminum housing, internal BPA free varnish, valve P14105) in the presence of propellant gas (butane), in a weight ratio composition/propellant gas 95/5.

Comparative device no 2: pump bottle
The composition above is packaged in a pump bottle type foamer.

Protocol:
0.8 g of the composition F in the form of foam is obtained from the two devices, device no 1 and device no 2.

The composition F in the form of foam obtained from the two devices is applied to locks of wet natural blond hair (tone depth 10, 4.5 g, 10 cm high). The locks of natural blond hair were previously washed with a shampoo and a standard conditioner.

The quantity of foam composition is applied on the top of the locks of hair.

The foam composition is then spread by combing the locks of hair from the top to the bottom of the hair with a fine comb.

The locks of hair are pre-dried with a hair-drier for 1 minutes, then completely dried and brushed, using a round brush.

Figure 1:
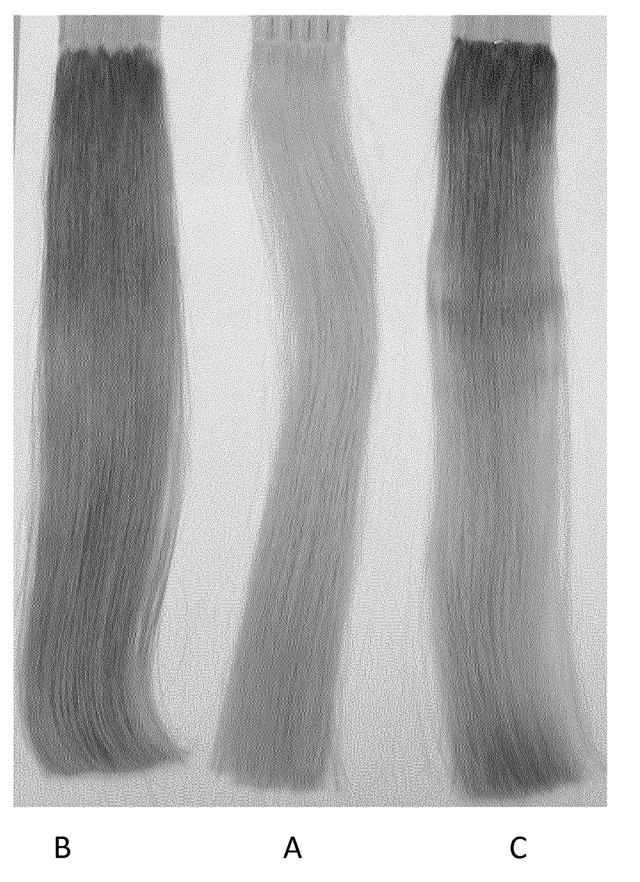
FIG. 1 is a photography of locks of hair treated with a composition obtained with two different devices as explained in example 4.

Finally, the locks of hair treated with composition F are hanging vertically and are photographed (see FIG. I).

Results:
The uniformity of the coloured coating is evaluated on the picture of the locks of hair on FIG. I (the lock of hair A in the center of FIG. I corresponds to a lock of hair before applying composition F).

With the aerosol device according to the invention (device no 1, lock B in FIG. I), the lock of hair presents a uniform coloured coating.

With the pump bottle (comparative device 2, lock C in FIG. I), the lock of hair does not present a uniform coloured coating.

The lock of hair treated with the foam obtained by the aerosol device according to the invention has a uniform coloured coating compared to the lock of hair treated with the foam obtained by the comparative device, pump bottle (device no 2).

The invention claimed is:

1. An aerosol device comprising:
a pressurized container comprising;
at least one propellant;
and
a composition comprising:
an aqueous medium;
at least one hybrid, film-forming, hydrophobic acrylic polymer;
at least one silicone compound chosen from linear silicone block copolymers, amino silicones, or mixtures thereof; and
at least one pigment; and
a dispensing valve disposed on the pressurized container.

2. The device of claim 1, wherein the at least one hybrid, film-forming, hydrophobic acrylic polymer and the at least one silicone compound are in the form of particles dispersed in the aqueous medium.

3. The device of claim 2, wherein:
the at least one silicone compound comprises a linear silicone block copolymer; and
the linear silicone block copolymer is obtained, in the presence of a catalyst, by a chain-extension reaction between:
a polysiloxane having one or more reactive groups; and
an organosilicone compound.

4. The device of claim 3, wherein the polysiloxane is chosen from compounds of formula (I):

wherein:
$R_1$ and $R_2$ are independently chosen from a hydrocarbon group having from 1 to 20 carbon atoms, an aryl group, or a reactive group, provided that there are on average from one to two reactive groups per polysiloxane molecule; and
n is an integer greater than 1.

5. The device of claim 4, wherein at least one of $R_1$ and $R_2$ is chosen from a hydrogen atom, an aliphatically unsaturated group, a hydroxyl group, an alkoxy group, an alkoxyalkoxy group, an acetoxy group, an amino group, or mixtures thereof.

6. The device of claim 4, wherein at least 80% of $R_1$ groups are methyl groups.

7. The device of claim 4, wherein $R_2$ at a chain end of the polysiloxane molecule is a vinyl group.

8. The device of claim 3, wherein the organosilicone compound is chosen from:
polysiloxanes of formula (I):

wherein:
$R_1$ and $R_2$ are independently chosen from a hydrocarbon group having from 1 to 20 carbon atoms, an aryl group, or a reactive group, provided that there are on average from one to two reactive groups per polysiloxane molecule; and
n is an integer greater than 1; or
compounds acting as chain extenders.

9. The device of claim 3, wherein the organosilicone compound is chosen from liquid organohydropolysiloxanes of formula (II):

(II)

wherein n is an integer ranging from 2 to 100.

10. The device of claim 1, wherein the at least one silicone compound comprises a divinyl dimethicone/dimethicone copolymer.

11. The device of claim 1, wherein the composition comprises at least one amino silicone chosen from compounds of formula (I):

$(R_1)_a(T)_{3-a}\text{-Si}[OSi(T)_2]_n\text{-}[OSi(T)_b(R_1)_{2-b}]_m$
$-OSi(T)_{3-a}\text{-}(R_1)_a$ wherein:
T is chosen from a hydrogen atom, a phenyl radical, a hydroxyl radical, a $C_1$-$C_8$ alkyl radical, or a $C_1$-$C_8$ alkoxy radical;
a is 0, 1, 2, or 3;
b is 0 or 1;
n is an integer from 49 to 149;
m is an integer from 1 to 10;
(n+m) ranges from 50 to 150;
$R_1$ is a monovalent radical of formula $-C_qH_{2q}L$, wherein q is a number from 2 to 8, wherein one or more of the hydrogen atoms may be optionally replaced by a hydroxyl group; and
L is an optionally quaternized amino group chosen from:
$-N(R^2)-CH_2-CH_2-N(R^2)_2$;
$-N(R^2)_2$;
$-N^+(R^2)_3Q^-$;
$-N^+(R^2)(H)_2Q^-$;
$-N^+(R^2)_2HQ^-$; or
$-N(R^2)-CH_2-CH_2-N^+(R^2)(H)_2Q^-$, wherein:
$R^2$ is hydrogen, a phenyl group, a benzyl group, or a saturated monovalent hydrocarbon radical, and
$Q^-$ is a fluoride, chloride, bromide, or iodide anion.

12. The device of claim 1, wherein the composition comprises at least one amino silicone chosen from compounds of formula (II):

(II)

wherein:
R, R' and R" are independently chosen from a $C_1$-$C_4$ alkyl radical, a $C_1$-$C_4$ alkoxy radical, or an OH radical;
A is a linear or branched $C_3$-$C_8$ radical;
m and n are integers; and
(m+n) ranges from 1 and 2000.

13. The device of claim 1, wherein the at least one amino silicone is chosen from compounds of formula (III) below:

(III)

wherein:
A is a linear or branched $C_2$-$C_8$ alkylene radical;
$R_1$ and $R_2$ independently represent a $C_1$-$C_4$ alkyl radical, a $C_1$-$C_4$ alkoxy, radical, or a hydroxyl radical; and
m and n are integers such that the weight-average molecular weight of the compound of formula (III) is greater than or equal to 75,000 g/mol.

14. The device of claim 1, wherein the composition comprises, based on the total weight of the composition:
0.1% to 20% by weight of silicone compounds;
0.1% to 30% by weight of hybrid, film-forming, hydrophobic acrylic polymers; and
0.01% to 30% by weight of pigments.

15. The device of claim 1, wherein the at least one hybrid, film-forming, hydrophobic acrylic polymer is synthesized from:
monomers having at least one optionally salified (meth)acrylic acid group, esters thereof, and/or amides thereof; and
monomers from at least one styrene compound.

16. The device of claim 1, wherein the at least one hybrid, film-forming, hydrophobic acrylic polymer is chosen from styrene/(meth)acrylate copolymers resulting from the polymerization of styrene monomers and $C_1$-$C_{10}$ alkyl (meth)acrylate monomers.

17. The device of claim 1, wherein the at least one hybrid, film-forming, hydrophobic acrylic polymer is chosen from styrene/(meth)acrylate copolymers resulting from the polymerization of styrene monomers, optionally salified (meth)acrylic acid monomers, and $C_1$-$C_{10}$ alkyl (meth)acrylate monomers chosen from methyl acrylate, ethyl acrylate, propyl acrylate, butyl acrylate, hexyl acrylate, octyl acrylate, or 2-ethylhexyl acrylate monomers.

18. The device of claim 1, wherein the composition comprises at least one hybrid, film-forming, hydrophobic acrylic polymer obtained by a polycondensation process from monomers having optionally salified (meth)acrylic acid groups, esters thereof, and/or amides thereof.

19. The device of claim 1, wherein:
the container has rigid walls and directly contains the composition; and
the at least one propellant is chosen from hydrocarbon-based gases containing from 2 to 6 carbon atoms.

20. A process for dyeing hair comprising:
applying a composition dispensed from an aerosol device to the hair; and
optionally drying the hair after applying the composition;
wherein the aerosol device comprises:

a pressurized container comprising the composition and at least one propellant; and
a dispensing valve disposed on the pressurized container; and wherein the composition comprises:
an aqueous medium;
at least one hybrid, film-forming, hydrophobic acrylic polymer;
at least one silicone compound chosen from linear silicone block copolymers, amino silicones, or mixtures thereof; and
at least one pigment.

* * * * *